(12) United States Patent
Ferguson et al.

(10) Patent No.: US 6,742,440 B2
(45) Date of Patent: Jun. 1, 2004

(54) SERVO-CONTROLLED INTEGRAL STOP FOR USE WITH A SERVO-CONTROLLED HYDRAULIC PISTON

(75) Inventors: Hugo S. Ferguson, Clearwater, FL (US); Wei Chang Chen, Wynantskill, NY (US)

(73) Assignee: Dynamic Systems, Inc., Poestenkill, NY (US)

( * ) Notice: Subject to any disclaimer, the term of this patent is extended or adjusted under 35 U.S.C. 154(b) by 0 days.

(21) Appl. No.: 10/439,474

(22) Filed: May 16, 2003

(65) Prior Publication Data

US 2003/0217639 A1 Nov. 27, 2003

Related U.S. Application Data

(60) Provisional application No. 60/382,637, filed on May 22, 2002.

(51) Int. Cl.⁷ .................................................. F15B 15/24
(52) U.S. Cl. ......................................... 92/13.1; 92/13.7
(58) Field of Search .................................. 92/13.1, 13.7

(56) References Cited

U.S. PATENT DOCUMENTS

| | | | |
|---|---|---|---|
| 2,715,389 A | * | 8/1955 | Johnson ...................... 92/13.1 |
| 5,092,179 A | | 3/1992 | Ferguson |
| 5,195,378 A | | 3/1993 | Ferguson ...................... 73/790 |
| 5,429,484 A | * | 7/1995 | Honda et al. ................. 92/13.7 |

FOREIGN PATENT DOCUMENTS

| DE | 23 45 445 | 3/1975 |
|---|---|---|
| DE | 29 43 332 | 5/1981 |

* cited by examiner

Primary Examiner—Edward K. Look
Assistant Examiner—Michael Leslie
(74) Attorney, Agent, or Firm—Michaelson & Associates; Peter L. Michaelson

(57) ABSTRACT

Apparatus, and an accompanying method for use therein, that utilizes working and stopping servo-controlled hydraulic pistons wherein the stopping piston acts as a controlled mechanical stop for the working piston. Both pistons are spaced apart along and coaxially arranged around a common shaft, with each piston moving in a separate cylinder. The working piston is securely attached to the shaft, while the shaft moves through a central, longitudinal bore of the stopping piston. The stopping piston effectively "floats" in its cylinder and produces a greater force than the working piston. A radially extending stop element, situated on the shaft, has a surface configured to abuttingly engage with a complementary surface on the stopping piston such that the stopping piston, once appropriately positioned, controllably stops continued movement of the working piston in a very short time and over a very short distance with little strain induced in the apparatus.

14 Claims, 3 Drawing Sheets

SERVO-CONTROLLED INTEGRAL STOP FOR USE WITH A SERVO-CONTROLLED HYDRAULIC PISTON

CLAIM TO PRIORITY

This application claims priority of our United States provisional patent application entitled "SERVO-CONTROLLED INTEGRAL STOP FOR SERVO-CONTROLLED PISTON IN HYDRAULIC SYSTEMS", filed May 22, 2002 and assigned serial No. 60/382,637; which is incorporated by reference herein.

BACKGROUND OF THE INVENTION

1. Field of the Invention

The invention relates to apparatus, and an accompanying method for use therein, that utilizes first (working) and second (stopping) servo-controlled hydraulic pistons wherein the second piston acts as a controlled mechanical stop for the first piston. Advantageously, the apparatus can controllably stop the first piston, traveling at relatively high speeds, in a very short time and over a very short distance while advantageously inducing very little, if any, elastic strain into the apparatus.

2. Description of the Prior Art

Metallic materials play an indispensable role as an essential component of an enormous number of different products. Such materials are produced typically in large ingots or other shapes and are controllably deformed by, e.g., rolling, forging or extruding into readily useable and conventional sheet, plate, coil or wire form for subsequent machining or forming. These deformations typically occur on a repeated incremental basis, such as through a multi-stand rolling mill where the material is repeatedly passed through successive pairs of rolls. Each pass incrementally compresses, i.e., deforms, the material into thinner stock. Typically, each pair of rolls is spaced equal distance from the next pair but has a smaller inter-roll spacing ("roll bite") than the next pair. Hence, as the material becomes thinner it travels at a faster rate through successive roll pairs and this decreases the time occurring between each compression. Extrusion, forging and braking operations also typically involve incremental deformations until the material is properly sized.

In production environments, small incremental deformations are typically produced at high rates. However, correctly configuring a mill, forge or brake to properly deform production stock and impart a desired amount of strain to the material along with other physical/metallurgical characteristics can be a tedious, time-consuming and expensive process—particularly since such a machine needs to be taken out of productive use for an extended time to properly adjust its operational parameters. Consequently, to avoid the need for costly downtime, thermodynamic material testing systems are employed to simulate rolling, extruding, braking and forging processes on relatively small metallic specimens. Resulting simulation data is then used to properly set various operating parameters of production equipment and, by doing so, minimize its non-productive downtime. Illustrative simulators of this type include the "Gleeble" and "Hydrawedge" systems manufactured by Dynamic Systems Inc. (DSI) of Poestenkill, N.Y., which is the present assignee hereof (with "Gleeble" and "Hydrawedge" being registered trademarks owned by DSI).

Systems which deform metallic materials, particularly including material testing systems, often utilize linear motion of a piston/anvil combination produced by servo-controlled hydraulic systems, and particularly those which accelerate and stop pistons at very high speeds. Such movement is necessary to impart a desired amount of deformation to the material, situated, e.g., between a pair of anvils, at a desired strain rate and over as much of a resulting deformation as possible. In these environments, linear piston systems moving with velocities up to 10 meters per second are frequently used, with velocities of 1 to 2 meters per second being quite common.

In particular, in such testing systems, a fundamental problem arises in that a piston, while traveling at such a high relative velocity, must often be stopped in a manner, essentially immediately, through which its velocity does not decrease even over a small distance, else the strain rate imparted to the specimen will decrease over a stopping distance of the piston. Further, those systems typically utilize mechanical mechanisms of one sort or another to stop the piston which, while the piston is being stopped, disadvantageously introduce some strain into various structural components of the system itself. This added strain, by effectively compressing a frame of the system, tends to slightly elongate the stopping distance and thus adversely impact the resulting deformation of the specimen.

Another area in which high-speed deformation is becoming increasingly important is sheet metal processing. Here, a need to reduce production costs requires that press brakes used to deform metallic material, i.e., bend metal sheets, operate at increasingly high speeds. Conventional bending machines have a set of shaped dies in which the material is held and then formed or bent. The dies are mounted in rather large, heavy beam structures. Usually, one beam is mounted rigidly, while another is mounted on linear sliding ways. Traditional brakes rely on producing linear motion for the ways through a large flywheel and suitable connecting/ pivoting arms mounted between one beam and the flywheel. Relatively modern brakes control the motion of the die/beam using hydraulic servo-controlled piston/cylinder systems. A precision with which the material can be bent depends upon how quickly the die can be stopped at a bottom of its stroke (travel). As the speed of the die increases, its stopping distance becomes increasingly arbitrary. Given this, the stroke often has to be disadvantageously run at a decreased speed to consistently stop the die at a precise location. Additionally, the metal being deformed often provides a variable load to the die. This variable load causes the control system to compensate while the dies are being stopped at a desired position, but again generally necessitates that reduced speeds are used to obtain precise bends in pieces then being processed. Such decreased speeds disadvantageously reduce material throughput. Hence, to consistently deform material at relatively high speeds and increase throughput, the stroke has to be accurately controlled both in terms of its velocity, throughout the stroke length, as well as its stopping distance.

In situations, be it in material testing systems or in production equipment, where material is being deformed at high-speeds, mechanical stops are often used to stop a high-speed anvil, ram or die at a precise position. Unfortunately, a position of such a mechanical stop has to be changed each time the desired amount of travel is changed.

Therefore, apparatus is needed to stop motion of, e.g., an anvil, a ram or die in an exact position even at very high speeds in order to provide consistent results. Such a stop should impart very little, if any, strain in the apparatus so that the stopping position remains the same regardless of the changes in a load then being deformed. This entails that an end of a high-speed stroke must be precisely controlled as well as being easily and rapidly changeable.

U.S. Pat. No. 5,092,179 (issued to H. S. Ferguson on Mar. 3, 1992) describes one such thermodynamic material testing system. As shown in FIG. 5 thereof, a stroke of piston 509 and shafts 540 and 545 are stopped by stop disc 543. A position of specimen material 570, being deformed, is advanced by hydraulic cylinder 590, piston 592, wedge combination 585/582, shaft 575, load cell 574, plate 568, anvil base 565 and anvil 560'. Each time specimen 570 is advanced by the wedge combination toward the left, anvil 560 is retracted and then rapidly advanced to the right, thus deforming specimen 570 until stop plate 543 hits cross-stop 550. A drawback inherent in this system is that, during each hit, an amount of strain occurs elastically in an entire wedge assembly that supports a load on the right side of the specimen (load cell side). This elastic strain allows anvil 560 to move in the direction of deformation, thus decreasing the amount of deformation in the specimen and slightly compromising a final thickness of the specimen after each deformation. Once the system has been used to deform a particular specimen at a certain temperature, a computer-controlled deformation schedule (deformation program) that controls the system can be modified to accommodate for expected loss (increased material thickness) in deformation that would result from the elastic strain. However, doing so is a passive correction and never exact. For multiple deformations involving 3 or more hits to the specimen, appropriate modifications to the program become time-consuming and tedious to determine. Further, each hit becomes less precise as the number of hits increases. Therefore, a stopping mechanism is readily desired, for use in a thermodynamic material testing system, that imparts very little, if any, strain back into any structural component of the system itself during each hit.

Thus, the need still exists in the art for a stopping mechanism for use with a servo-controlled hydraulic system, such as that used in a material testing system, in which a piston can be stopped from a very high speed at an exact location without over-travel and without substantial reduction in its speed right up to the moment of its stopping. The system should be capable of repetitive hits with each final stop at a predetermined position regardless of the speed of the piston. The stopping system should produce very little, if any, strain.

Further evidence for the need for such a stopping mechanism can be seen from the following. A modern high-speed servo valve can be closed, from 80 percent of its maximum opening, typically in 0.003 seconds. If a piston controlled by that valve is moving at 1 meter per second—which often occurs in production equipment and material testing systems, then the piston will travel approximately 1.5 mm during stopping. This distance is clearly unacceptable where, in testing systems and high-speed press brakes, distances controlled to less than 0.05 mm are desired. Linkages, shafts and wedges of existing stopping mechanisms can have strains, under expected operating loads, of 0.3 or 0.4 mm. While these reduced strains are considerably better than that which results from use of no stopping mechanism at all, a stopping mechanism that produces far less strain in the mechanism itself is still needed.

SUMMARY OF THE INVENTION

The present invention advantageously overcomes the deficiencies associated with high-speed use of servo-controlled hydraulic systems known in the art where very rapid stopping is required with essentially little, if any, strain occurring in the stopping mechanism. Through the invention, a first high-speed (working) piston is stopped by an adjustable mechanical stop, formed of a second (stopping) piston coaxially situated to the working piston.

Advantageously, the present invention permits the stopping position of the working piston to be rapidly changed. Furthermore, the invention, by virtue of its stopping characteristics and inducing minimal resulting strain in the stopping mechanism, permits the servo system to repetitively and rapidly actuate the working piston, many times, with nearly ideal stopping positions each time regardless of the speed of that piston. High-speed stopping occurs over extremely short stopping distances and is essentially immediate.

In accordance with the teachings of the invention, the working and stopping pistons are controlled by separate servo-control hydraulic systems and are both coaxially located on a common piston shaft for the working piston, with these pistons being longitudinally spaced apart on the shaft. Both pistons controllably move within separate corresponding piston cylinders. The stopping piston slides on the piston shaft with the shaft extending through a central longitudinally-oriented bore on the stopping piston. To stop further movement of the working piston, the stopping piston abuttingly engages, via complementary surfaces, with a radially extending circular stopping element on the shaft, e.g., a shoulder extending outward from and concentric with the shaft. Preferably and to provide positive stopping action, the stopping piston is sized and operated with sufficient hydraulic pressure to provide higher forces than the working piston. Illustratively, the working piston may provide a maximum force of 40 tons and the stopping piston a maximum force of 80 tons or more.

In operation, the stopping piston is programmably moved, through appropriate computer-control of its servo-control hydraulic system, to a desired stopping position for the working piston. The working piston is retracted (before, coincident with or after the stopping piston is moved) and, once the stopping piston is properly position, then extended at a high speed. The working piston stops its extension whenever a surface of the stopping element on the piston shaft abuttingly engages a complementary surface situated on an upper side of the stopping piston. To change the stopping position, the stopping piston is simply moved, again through appropriate control over the servo-controlled hydraulic system, and the process is repeated, and so forth for multiple hits.

The stopping mechanism is comprised of only the stopping piston and hydraulic oil used to position that piston. There are no stopping linkages, wedges, shafts or other mechanical parts which would change dimension under a changing load. Accordingly, the amount of strain that occurs in the stopping mechanism is significantly reduced.

In accordance with a feature of the invention, two stopping elements (i.e., upper and lower stopping elements) can be positioned on the piston shaft, with a corresponding stopping element situated on either side of the stopping piston. In this manner, and with complementary surfaces being formed on the upper and lower surfaces of that piston, the stopping piston can stop movement of the working piston in both its upward and downward (retraction and extension) directions, rather than just in a downward direction.

BRIEF DESCRIPTION OF THE DRAWINGS

The teachings of the present invention can be readily understood by considering the following detailed description in conjunction with the accompanying drawings, in which.

DETAILED DESCRIPTION

After considering the following description, those skilled in the art will clearly realize that the broad teachings of the invention can be readily utilized in conjunction with any one of a wide variety of applications that rely on high-speed motion of hydraulic pistons where such a piston must be reliably, consistently and accurately stopped in minimal distance without inducing undue strain in a stopping mechanism (and, through it, e.g., into structural components of a mechanical device inter-connected thereto). Such applications illustratively include high-speed press brakes and thermodynamic material testing systems which simulate, e.g., rolling mills, extruders and hammer forges.

Figure 1:
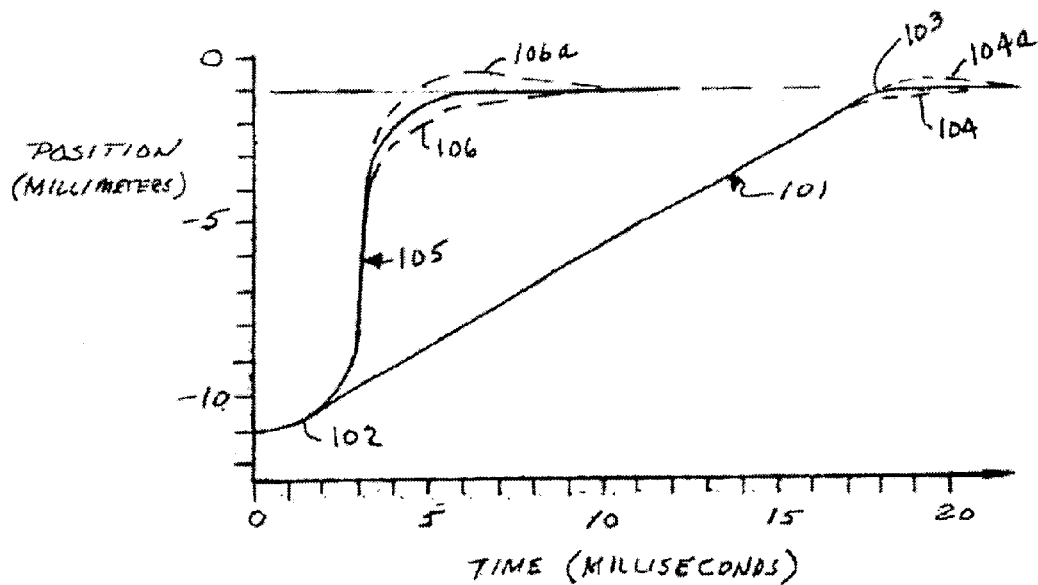
FIG. 1 graphically depicts typical curves 101 and 105 that represent a path of a piston during relatively low- and high-speed travel, respectively, such as would occur in a press brake or a thermodynamic material testing system, with, as shown, travel velocity being decreased at an end of piston travel to obtain correct travel distance and stopping position.

FIG. 1 graphically depicts typical curves 101 and 105 that represent a path of a piston (not specifically shown) during relatively low- and high-speed travel, respectively, as would typically occur in a press brake or a thermodynamic material testing system.

As shown, curve 101 depicts a relatively slow travel path (in millimeters) of a servo-controlled hydraulic piston as a function of time (in milliseconds). Curved portions 102 and 103 occur as a result of time intervals that are required to start the piston in motion and to stop it, respectively. Start and stop times of a servo system are dependent upon a response of an hydraulic servo valve, inertia of the system and tuning of conventional PID (proportional, integral and differential) settings of a servo loop contained within the system. The PID settings often have to be adjusted as a maximum speed of the piston increases.

Dashed lines 104 and 104a indicate possible initial positional deviation expected for the stopping position of the piston. Specifically, dashed line 104 represents possible positional under-shoot, while dashed line 104a represents possible positional over-shoot of the piston. Clearly, the under-shoot is of little consequence in a deformation process as long as the piston eventually corrects its position to a desired value. The precision to which the piston will reach the exact desired position depends upon a value of the P (proportional or system gain) setting of the PID terms. Usually, as the value of the P term increases, the closer will the final position of the piston be to the desired value. However, also, as the value of P increases, so too will a likelihood that the servo system will oscillate. Consequently, the final setting of the P term is usually a compromise. As such and on one hand, during relatively slow-speed travel, a final piston position can become extremely close to its desired value at an end of its programmed travel. On the other hand, during high-speed travel, the final piston position may be very close to its final programmed value but is rarely, if ever, exactly equal to it. In that regard, during high-speed travel, a relatively small amount of time and therefore distance is required for the piston to reach the desired position, but, owing to mechanical delays and other mechanical response characteristics of the hydraulic servo system, the piston will typically over-shoot its desired final position (as indicated by dashed portion 104a).

Curve 105 depicts a relatively high-speed travel path of the servo-controlled piston as a function of time. Positional under-shoot 106 and positional over-shoot 106a are larger than those for the low-speed travel depicted by curve and the over-shoot may include some oscillation (also not shown but well known). If the piston is being used to move a ram or anvil to compressively deform a specimen, as would be the case in a thermodynamic material testing system, then positional over-shoot causes undesired deformation of the specimen and imparts excessive strain in the specimen. Should the piston move, e.g., a die on a hammer brake, then in bending sheet metal, the over-shoot would over-bend the metal.

Figure 2:
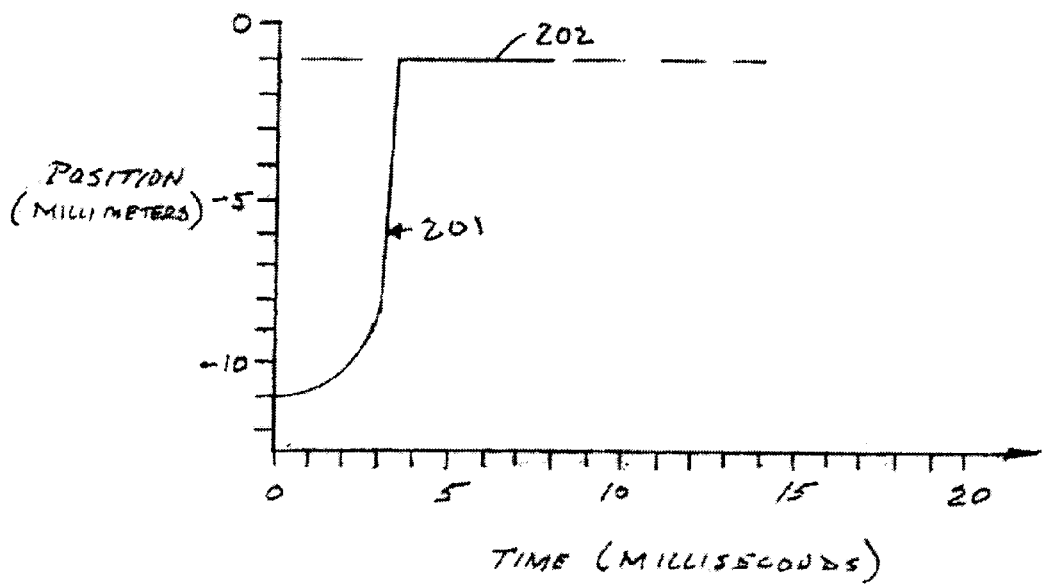
FIG. 2 graphically depicts curve 201 corresponding to curve 101, shown in FIG. 1, but with a significantly increased travel speed and appreciably reduced stopping distance, both possible through use of the present inventive mechanical stop.

FIG. 2 graphically depicts curve 201, corresponding to curve 101 shown in FIG. 1, but with a significantly increased travel speed and appreciably reduced stopping distance, both achievable through use of the present inventive mechanical stop.

Here, FIG. 2 depicts a relatively high-speed travel path 201 (in millimeters) as a function of time (in milliseconds) for the piston as well as a rapid stopping position 202, where a high-speed (first) piston hits a mechanical stop implemented by a second (stopping) piston as taught by the present invention. The servo control of the first piston is not required after reaching position 202, because the second piston prevents the first piston from further travel. The PID setting of the servo system that controls movement of the first piston is far less important here, as that servo system is no longer in control of this piston once it hits the second piston. The second piston overpowers and, for all practical purposes, immediately stops further movement of the first piston, since the second piston provides much higher forces that the first piston.

By virtue of providing what is effectively an immediate and abrupt stop (indicated by line 202), the present invention permits the first piston to advantageously operate at a considerably increased travel speed (as indicated by he nearly vertical section of curve 201) over that associated with a upwardly sloped central portion of curve 101 shown in FIG. 1.

Figure 3:
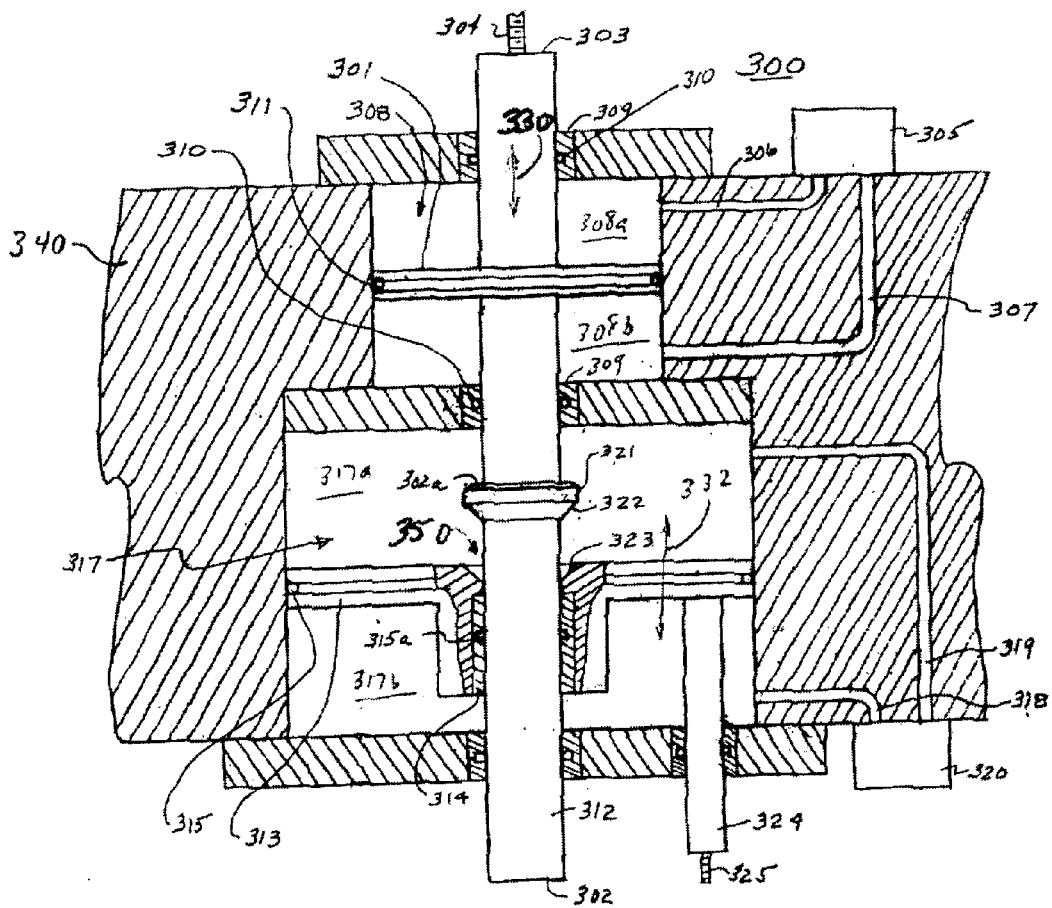
FIG. 3 depicts, in cut-away sectional view, first embodiment 300 of the present invention, here for stopping movement of working piston 301 in its downward direction (extension)

FIG. 3 depicts, for clarity in cut-away sectional view, first embodiment 300 of the present invention, here for stopping movement of working piston 301 in its downward direction (extension).

Figure 4:
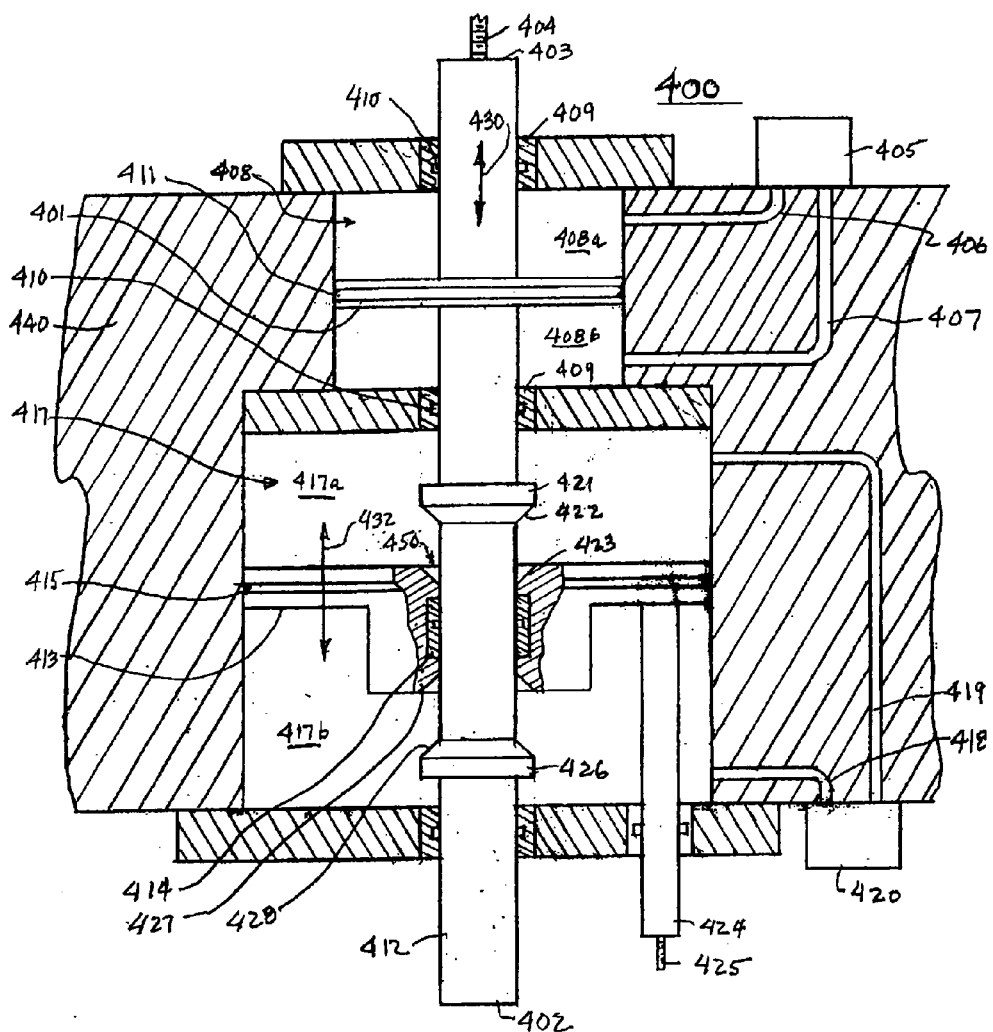
FIG. 4 depicts, also in cut-away sectional view, second embodiment 400 of the present invention, here for stopping movement of working piston 401 in both its upward and downward directions (extension and retraction).

Housing 340 contains two hydraulic cylinders 308 and 317 oriented in a tandem configuration. For simplicity, while the housing, for each of the embodiments shown in FIGS. 3 and 4, is formed of several structural pieces, the fasteners (which are readily apparent to those skilled in the art) used to secure these pieces together, along with all appropriate seals, have been intentionally omitted for simplicity.

First (working) piston 301 controllably moves bi-directionally within cylinder 308 in the directions (extension and retraction) indicated by arrow 330. This piston is integral to piston shaft 312 which extends from end locations 302 to 303. Shaft 312 is formed of two pieces (not specifically labeled) for ease of assembly. These two pieces are assembled (specifically screwed) together, via a large screw and thread, with an alignment ring (not shown) at joint line 302a. Threaded extension screw 304 emanating from shaft 312 and particularly end location 303 extends to a suitable, conventional linear displacement transducer (not shown) to measure a current position of piston 301. This transducer is connected to a servo controller and programmer (conventional and also not shown). Inasmuch as both the servo controller and programmer are conventional and well-known in the art, neither will be discussed in any further detail hereinafter. A position signal from the transducer is applied, as a position feedback signal, to the servo controller which, in turn, controls servo valve 305.

Valve 305 directs pressurized hydraulic fluid (hydraulic oil) supplied by a suitable, conventional hydraulic pump (not shown), via conduits 306 and 307, into one of cylinder regions 308a and 308b and out of the other. As depicted and within cylinder 308, region 308a lies above working piston 301; while cylinder region 308b lies below it. The specific region that is to receive fluid (and correlatively the region that is to lose fluid), and hence the direction of the flow of the fluid through the conduits, is determined by the servo controller based on whether working piston 301 is to be extended (moved upward) or retracted (moved downward). The opening of the valve determines a rate at the fluid enters one cylinder region and leaves the other and hence a speed at which working piston 301 moves. The time during which the valve remains open, in conjunction with the size of the valve opening, determines the final position of the piston within the cylinder. Cylinder 308 is sealed at both ends by suitable seals and bearings 309 and 310 (identical seals and bearings, not specifically labeled, are also used at a distal end of cylinder 317). Piston 301 has suitable seals 311 to separate cylinder regions 308a and 308b from each other.

Second (stopping) piston 313 has central longitudinal bore 350 through which this piston is coaxially mounted on and controllably moves (specifically slides), in a direction given by arrow 332, along piston shaft 312. This piston moves within cylinder 317 that contains cylinder regions 317a and 317b. As depicted, regions 317a and 317b are respectively situated above and below stopping piston 313. Bearing 314 and seals 315 and 315a separate cylinder regions 317a and 317b from each other.

Cylinder regions 317a and 317b are connected to servo valve 320 via conduits 319 and 318, respectively, to servo valve 320. Servo valve 320 is also connected to a suitable hydraulic pump and a second (stop position) servo controller (not shown). As with cylinder elements 308a and 308b, the specific region 317a or 317b that is to receive fluid (and correlatively the region that is to lose fluid), and hence the direction of the flow of the fluid through the conduits, is determined by the stop position servo controller based on whether stopping piston 313 is to be extended (moved upward) or retracted (moved downward). The opening of valve 320 determines a rate at the fluid enters one cylinder region and leaves the other and hence a speed at which stopping piston 313 moves. The time during which the valve remains open, in conjunction with the size of the valve opening, determines the final position of the piston within the cylinder.

Shaft 324, connected to stopping piston 313, is itself connected via threaded extension screw 325 to a suitable (second) linear displacement transducer (not shown) that provides a feedback signal indicative of a current position of the stopping piston 313. This position information is fed to the second (stop position) servo controller/programmer to control the current position of stopping piston 313.

A load for compression work, e.g., a ram or anvil, is attached to shaft 312 at its end 302. Stopping piston 313 is not connected to any external work and is used only to stop piston shaft 312 at a predetermined desired position, and hence produces no output working force to, e.g., an anvil, ram or die or similar device. The stopping piston basically "floats" in cylinder 317.

Circularly-shaped coaxial, radially expanded section (element) 321 (here forming a shoulder), having lower face 322, is rigidly, securely and integrally formed on shaft 312 as a stop element. This section is intentionally shaped to be too large to pass through central bore 350 of stopping piston 313 and hence must stop whenever shoulder 322 (here being a lower face) of element 321 abuts against upper face 323 of stopping piston 313. Lower face 322 and upper face 323 are shaped in a complementary fashion to each other. Stopping piston 313 is usually larger in size than is piston 301 in order to over-power and precisely limit the travel of working piston 301 and shaft 312. For example, when both cylinders 308 and 317 are equally pressurized with hydraulic fluid, working piston 301 may produce a maximum force of 40 tons, while stopping piston 313, which stops the travel of working piston 301, may produce a maximum force of 80 or more tons. Advantageously, the larger the maximum force capability of stopping piston 313, the stiffer the stop will be and accordingly the more precise the stopping position of working piston 301 will be. Further, an amount of hydraulic oil that supports stopping piston 313 also contributes to stopping error due to compressibility of the oil. Hence, that amount should be minimized. But, as will be seen below, the stopping mechanism can be readily set to compensate for this error.

Since both pistons 301 and 313 are individually controlled as to their positions, the position of stopping piston 313 may be changed at any time. If working piston 301 is retracted (moves upward in a distal direction from piston 313), then stopping piston 313 can move independently of the working piston. If the working piston is in abutting contact, along faces 322 and 323, with the stopping piston, then moving stopping piston 313 upwardly will also move working piston 301 in the same manner and by the same amount. Conversely, attempting to move working piston 301 downward, while the stopping piston is being held in its current position, will not be possible inasmuch as stopping piston 313, which is larger than the working piston and correlatively produces a larger force, cannot be over-powered by the working piston. In normal operation, working piston 301 would be retracted away from stopping piston 313 before the latter piston is repositioned. Thereafter, working piston 301 is extensibly driven downward until stopping element 321 runs directly up against stopping piston 313, and faces 322 and 323 engage and abut against with each other, at which point any further downward movement of working piston 301 and shaft 312, for all practical purposes, immediately halts.

As shown, face (stopping surface) 322 of stopping element 321 advantageously has a sloped surface as its stopping surface. The slope increases a surface area (over a surface which is perpendicular to a longitudinal axis of piston shaft 312) which contacts face (stopping surface) 323, the latter being identically sloped to match that of surface 322. The actual slope, i.e., angular incline, of these stopping surfaces is predefined but not critical as long as it is sufficiently large, given impact forces involved, to provide enough contact area to adequately reduce resulting contact pressure during stopping to a level that will not damage either of the faces but nevertheless provide effective stopping action.

As indicated, stopping piston 313 has no force output, since it has no piston shaft. The stopping piston may thus be considered to be "floating" in that it simply moves under control in cylinder regions 317a and 317b, but does not provide any force output. Shaft 324 is only used, coupled via screw thread 325 to a linear position transducer (not shown), to provide a corresponding position feedback signal and thus to provide a modality through which current position of stopping piston 313 can be measured.

In operation, servo valve 320 would be controlled, by its corresponding servo-controller and in a programmed fashion, to position stopping piston 313 to stop piston shaft 312 at a precise desired location. Servo valve 305, operating under control of its corresponding servo-controller, would then programmably cause working piston 301 and piston rod 312 to travel downward at the desired velocity until faces 322 and 323 abut against each other. If working piston 301 is controlled to move at a relatively high velocity, e.g., one or more meters per second, then the impact forces at faces 322 and 323 may be large.

Current, commercially available high-speed servo valves can operate in 3 to 6 milliseconds (i.e., change position by 80 percent, open or close). If piston shaft 312 were traveling at 1 meter per second, the distance of travel in just 3 milliseconds would be 3 millimeters. Some applications require that a working piston, e.g., working piston 301, be stopped within a small fraction of a millimeter (often 0.1 mm or less), while it is traveling at 1 meter per second or more. The relatively slow operation of such high-speed servo valves, as compared to a requirement to precisely stop the piston traveling at such a high speed in a very short distance, dictates the need for the inventive adjustable stop. The inventive stop mechanism advantageously fills that need. Moreover, the position of the stop, i.e., that of stopping piston 313, is completely adjustable using its corresponding stop position servo controller. The adjustment can be rapidly accomplished, using an appropriate high-speed servo control system, in order to permit high-speed operation of both pistons 301 and 313, and particularly multiple stopped retraction-extension cycles of working piston 301 in a relatively short time (so as to permit, e.g., a ram or anvil, to which end 302 of piston shaft 312 would typically be connected, in a thermodynamic material testing system to impart a series of rapidly occurring hits onto a specimen then being deformed).

FIG. 4 depicts, along in cut-away sectional view, second embodiment 400 of the present invention, here for stopping movement of working piston 401 in both its upward and downward directions (retraction and extension).

To facilitate understanding, highly similar reference numerals, with only a change in their first digit, have been used in FIGS. 3 and 4 to designate similar, if not identical, corresponding elements in these two figures. Given the commonality between the structures shown, only the differences therebetween will be specifically discussed. To implement bi-directional stopping, two separate stopping elements have been formed in piston shaft 412: element 421 situated above stopping piston 413 and element 426 situated below it. Both elements are formed as radially extended portions of piston shaft 412, having a sufficiently enlarged radius over that portion of the shaft which passes through central bore 450 of stopping piston 413, with sloping faces 422 and 428, respectively. These faces abuttingly engage, when working piston 401 is moving in an downward or upward direction, with complementary shaped sloped upper and lower faces 423 and 427, respectively, of stopping piston 413. Similar to shaft 312, shaft 412 is fabricated in sections and then appropriately screwed together using threaded sections.

Hence, stopping piston 413 can stop working piston 401 and piston shaft 412 by abutting contact along either faces 422 and 423, or faces 427 and 428. This permits high-speed stopping of working piston 401 and shaft 412 to occur in either direction of travel.

Some compression of the hydraulic oil in cylinder regions 417a and 417b (depending upon force and direction of travel of working piston 401) will occur when the force of working piston 401 is abruptly transferred to stopping piston 413 during a high-speed stop.

In both embodiments 300 and 400 shown in FIGS. 3 and 4, under known force conditions, an amount of compression of the hydraulic oil and resulting strain introduced into the parts of the system under load can be corrected by programming an amount of offset in the opposite direction, to the direction of travel of working piston 301 or 401 into the position of stopping piston 313 or 413, respectively, to offset or cancel this effect.

Though the present invention has been described in terms of using a single stopping piston to bi-directionally stop the working piston, the inventive stopping mechanism is not so limited. In that regard, two separately controllable upper and lower stopping pistons (each moving in its own cylinder) and again tandemly arranged (and each with its own position feedback transducer) can be substituted for single stopping piston 413 (and its cylinder 417) depicted in FIG. 4. Here, an upper stopping element could be situated above, i.e., outward of, the upper stopping piston (similar to the location of stopping elements 321 or 421 shown in either FIG. 3 or 4 relative to the stopping piston 313 or 413, respectively) and a lower stopping element situated below (again outward of) the lower stopping piston (similar to the location of stopping element 426 shown in FIG. 4 relative to stopping piston 413). Both stopping pistons would be situated on and moveable along the same piston shaft as the working piston. Such an arrangement permits the stops for both retraction and extension of the working piston to be separately set relative to each other. Alternatively, the stopping elements can be appropriately situated on the piston shaft inward (i.e., sandwiched between), rather than outward, of the two stopping pistons. Depending on a specific application, other orientations for the cylinders than those shown and described for the stopping and working pistons, such as being non-adjacent, could be used as well.

Furthermore, for the embodiment shown in FIG. 3, a single stopping element could be located on the piston shaft and situated below, rather than above, the stopping piston in order to stop movement of the working piston in just its upward direction (retraction).

In addition, while both embodiments utilize, for simplicity, a common piston shaft for both the working and stopping pistons, such a common shaft is not necessary. Other configurations can be used and, in fact, the shaft extending from the working piston towards the stopping piston can be different from that extending upward from the working piston. Moreover, the former shaft need not be a single shaft running through a central bore of the stopping piston but can instead be formed of one or more shafts, where each runs through a different bore in the stopping piston provided that one or more of these shafts has an appropriate stopping element situated on it.

Although various preferred embodiments which incorporate the teachings of our present invention have been separately shown and described in considerable detail herein, those skilled in the art can readily devise many other different embodiments that still incorporate the inventive teachings.

We claim:

1. Apparatus for providing a controlled mechanical stop that halts further movement of a first hydraulic piston, the apparatus comprising:
   the first hydraulic piston controllably moveable in a first piston cylinder, the first piston having a piston shaft attached to the first piston and extending outwardly therefrom;
   a second hydraulic piston controllably positionable in a second piston cylinder to a desired stopping position therein, said second cylinder being separate from the first piston cylinder and said second piston producing greater force than the first piston;
   the shaft extending longitudinally through a bore in second piston such that shaft can slidably move through the second piston; and
   a stopping element situated on the shaft such that during movement of the first piston and the shaft in a predefined direction, the stopping element will abuttingly engage with the second piston at the stopping position such the second piston will over-power and stop further movement of the shaft and the first piston in the predefined direction.

2. The apparatus recited in claim 1 wherein the first piston imparts an output working force to a device situated at an end of the shaft.

3. The apparatus recited in claim 2 wherein the shaft is common to both the first and second pistons and extends through a central longitudinal bore of the second piston.

4. The apparatus recited in claim 3 wherein the first and second pistons are coaxially arranged on the shaft and spaced apart from each other.

5. The apparatus recited in claim 4 wherein the first and second cylinders are arranged in tandem on the shaft with the first cylinder above the second cylinder, and the stopping element is situated on the shaft either between the first and second pistons or below the second piston.

6. The apparatus recited in claim 5 wherein the stopping element has a first stopping surface with a predefined orientation and the second piston comprises a second stopping surface with a complementary orientation to the predefined orientation of the first stopping surface, wherein the first and second stopping surfaces abuttingly engage with each other at the stopping position.

7. The apparatus recited in claim 6 wherein the first and second stopping surfaces are each sloped, at a predefined incline, relative to a longitudinal axis of the shaft.

8. The apparatus recited in claim 7 wherein the device is a ram, anvil or die.

9. The apparatus recited in claim 6 wherein the first and second cylinders are connected to separate corresponding first and second servo hydraulic valves, with the first and second valves being connected to and controlled by separate first and second corresponding servo controllers, wherein:
   the second servo controller actuates the second valve so as to position the second piston to the stopping position and then hold the second piston at the stopping position; and
   while the second piston is being so held, the first servo controller actuates the first valve to controllably extend or retract the first piston at a predetermined rate until such time as the first stopping surface abuttingly engages with the second stopping surface such that the second piston over-powers continued movement of the first piston and halts further extensile or retractile movement, respectively, thereof.

10. The apparatus recited in claim 9 wherein the first and second stopping surfaces are sloped, at a predefined incline, relative to a longitudinal axis of the shaft.

11. The apparatus recited in claim 10 wherein the device is a ram, anvil or die.

12. In apparatus for providing a controlled mechanical stop that halts further movement of a first hydraulic piston, the apparatus having:
   the first hydraulic piston controllably moveable in a first piston cylinder, the first piston having a piston shaft attached to the first piston and extending outwardly therefrom;
   a second hydraulic piston controllably positionable in a second piston cylinder to a desired stopping position therein, said second cylinder being separate from the first piston cylinder and said second piston producing greater force than the first piston;
   the shaft extending longitudinally through a bore in second piston such that shaft can slidably move through the second piston; and
   a stopping element situated on the shaft;
   a method comprising the steps of:
      moving the second piston to the stopping position and thereafter holding the second piston in said stopping position; and
      then moving the first piston at a predetermined rate and in a predefined direction until such time as the first stopping surface of the stopping element abuttingly engages with the second piston such that the second piston over-powers continued movement of the first piston and halts further movement thereof in the predefined direction.

13. The method recited in claim 12 wherein the first and second cylinders are connected to separate corresponding first and second servo hydraulic valves, with the first and second valves being connected to and controlled by separate first and second corresponding servo controllers, the method further comprising the steps of:
   actuating the second valve, through the second servo controller, so as to position the second piston to the stopping position and then hold the second piston at the stopping position; and
   while the second piston is being so held, actuating the first valve, through the first servo controller, to controllably extend or retract the first piston at a predetermined rate until such time as the first stopping surface abuttingly engages with the second stopping surface such that the second piston over-powers continued movement of the first piston and halts further extensile or retractile movement, respectively, thereof.

14. The method in claim 13 further comprising the step of imparting, through movement of the first piston, an output working force to a device situated at an end of the shaft.

* * * * *